United States Patent
Poznansky et al.

(10) Patent No.: US 11,547,694 B2
(45) Date of Patent: Jan. 10, 2023

(54) CXCR4/CXCR7 BLOCKADE AND TREATMENT OF HUMAN PAPILLOMA VIRUS-ASSOCIATED DISEASE

(71) Applicant: The General Hospital Corporation, Boston, MA (US)

(72) Inventors: Mark C. Poznansky, Newton Center, MA (US); Jeffrey Gelfand, Cambridge, MA (US); Sara Pai, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/496,821

(22) PCT Filed: Mar. 22, 2018

(86) PCT No.: PCT/US2018/023689
§ 371 (c)(1),
(2) Date: Sep. 23, 2019

(87) PCT Pub. No.: WO2018/175676
PCT Pub. Date: Sep. 27, 2018

(65) Prior Publication Data
US 2020/0030286 A1 Jan. 30, 2020

Related U.S. Application Data

(60) Provisional application No. 62/475,497, filed on Mar. 23, 2017, provisional application No. 62/503,988, filed on May 10, 2017.

(51) Int. Cl.
| | | |
|---|---|---|
| *A61K 31/395* | (2006.01) | |
| *A61P 35/00* | (2006.01) | |
| *A61K 35/17* | (2015.01) | |
| *A61K 51/10* | (2006.01) | |
| *A61K 39/12* | (2006.01) | |
| *A61K 39/395* | (2006.01) | |
| *A61K 39/00* | (2006.01) | |

(52) U.S. Cl.
CPC ............ *A61K 31/395* (2013.01); *A61K 35/17* (2013.01); *A61K 39/12* (2013.01); *A61K 39/3955* (2013.01); *A61P 35/00* (2018.01); *A61K 2039/505* (2013.01); *A61K 2039/585* (2013.01)

(58) Field of Classification Search
None
See application file for complete search history.

(56) References Cited

U.S. PATENT DOCUMENTS

| | | | |
|---|---|---|---|
| 4,501,729 A | 2/1985 | Boucher et al. | |
| 4,957,735 A | 9/1990 | Huang | |
| 5,075,109 A | 12/1991 | Tice et al. | |
| 5,272,082 A | 12/1993 | Santoli et al. | |
| 5,583,131 A | 12/1996 | Bridger et al. | |
| 5,858,358 A | 1/1999 | June et al. | |
| 5,883,223 A | 3/1999 | Gray | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,618,817 B2 | 11/2009 | Campbell | |
| 7,749,501 B2 | 7/2010 | Gelfand | |
| 8,034,332 B2 | 10/2011 | Klingemann | |
| 8,034,334 B2 | 10/2011 | Dudley et al. | |
| 8,143,387 B2 | 3/2012 | Gelfand | |
| 8,383,099 B2 | 2/2013 | Dudley et al. | |
| 8,906,682 B2 | 12/2014 | June et al. | |
| 2002/0068044 A1 | 6/2002 | Klingemann | |
| 2006/0121005 A1 | 6/2006 | Berenson et al. | |
| 2008/0247990 A1 | 10/2008 | Campbell | |
| 2008/0300165 A1 | 12/2008 | Poznansky et al. | |
| 2012/0321666 A1 | 12/2012 | Cooper et al. | |
| 2014/0065096 A1 | 3/2014 | Ichim et al. | |
| 2015/0216843 A1* | 8/2015 | Fearon ................. | A61K 31/713 424/174.1 |
| 2015/0352208 A1 | 12/2015 | Fearon | |
| 2016/0235779 A1 | 8/2016 | Marcus | |
| 2016/0304607 A1 | 10/2016 | Sadineni et al. | |
| 2018/0179282 A1* | 6/2018 | Cardarelli .......... | C07K 16/2827 |

FOREIGN PATENT DOCUMENTS

| | | |
|---|---|---|
| WO | 2004/037175 | 5/2004 |
| WO | WO 2013/154760 | 10/2013 |
| WO | WO 2014/055668 | 4/2014 |
| WO | WO 2016/201425 | 12/2016 |
| WO | WO 2017/009842 | 1/2017 |
| WO | WO 2017/019767 | 2/2017 |
| WO | WO 2017/156461 | 9/2017 |

OTHER PUBLICATIONS

Chen et al. Tannic Acid Is an Inhibitor of CXCL12 (SDF-1)/CXCR4 with Antiangiogenic Activity. Clinical Cancer Research, vol. 9, 3115-3123, Aug. 1, 2003.*
Chaudary et al. Plerixafor Improves Primary Tumor Response and Reduces Metastases in Cervical Cancer Treated with Radio-Chemotherapy. Clin Cancer Res; 1-8. Published OnlineFirst Oct. 3, 2016.*

(Continued)

*Primary Examiner* — Nianxiang Zou
(74) *Attorney, Agent, or Firm* — Fish & Richardson P.C.

(57) ABSTRACT

The present invention relates to methods and compositions for treating human papilloma virus (HPV)-associated diseases using an inhibitor of CXCL12 signaling. The invention further relates to methods and compositions for treating immune checkpoint blockade resistant diseases using an inhibitor of CXCL12 signaling. The invention further relates to methods and compositions for enhancing the immune response against an HPV-associated disease using an inhibitor of CXCL12 signaling.

13 Claims, 2 Drawing Sheets

(56) References Cited

OTHER PUBLICATIONS

E. D. Clercq. AMD3100/CXCR4 inhibitor. Frontirers in Immunology, 2015, vol. 6, article 276.*

International Search Report and the Written Opinion corresponding to International Application No. PCT/US2018/023689 dated Aug. 9, 2018.

Righi et al. "CXCL 12/CXCR4 Blockade Induces Multimodal Antitumor Effects that Prolong Survival in an Immunocompetent Mouse Model of Ovarian Cancer", Cancer Research 71(16):5522-5534 (2011).

Roden et al. "How will HPV vaccines affect cervical cancer?", Nat Rev Cancer 6(10):753-763 (2006).

Glienke et al., "Advantages and applications of CAR-expressing natural killer cells," Front.Pharmacol., Feb. 2015, 6, article 21, 7 pages.

Ho et al., "Interactions of Target-sensitive Immunoliposomes with Herpes Simplex Vims," J. Biol. Chem., Oct. 1987, 262(29):13979-13984.

Ho et al., "Target-sensitive Immunoliposomes as an Efficient Drug Carrier for Antiviral Activity," J. Biol. Chem., Oct. 1987, 262(29):13973-13978.

Ho et al., "Target-sensitive immunoliposomes: preparation and characterization," Biochemistry, Sep. 1986, 25(19):5500-5506.

Jaafar et al., "Correlation of CXCL12 Expression and FoxP3+ Cell Infiltration with Human Papillomavirus Infection and Clinicopathological Progression of Cervical Cancer," Am J Pathol, Oct. 2009, 175(4):1525-1535.

McDermott et al., "A phase 1 clinical trial of long-term, low-dose treatment of WHIM syndrome with the CXCR4 antagonist plerixafor," Blood, Apr. 2014, 123(15):2308-2316.

PCT International Preliminary Report on Patentability in International Application No. PCT/US2018/023689, dated Sep. 24, 2019, 6 pages.

Raeburn et al., "Techniques for drug delivery to the airways, and the assessment of lung function in animal models," J. Pharmacol. Toxicol. Meth., May 1992, 27(3):143-159.

Santini, Jr. et al., "A controlled-release microchip," Nature, 1999, 397:335-338.

Scott et al., "Monoclonal antibodies in cancer therapy," Cancer Immun., May 2012, 12:14.

Tyle, "Iontophoretic devices for drug delivery.," Pharm Res., 1986, 3(6):318-326.

Vianello et al., "Murine B16 Melanomas Expressing High Levels of the Chemokine Stromal-Derived Factor-1/CXCL12 Induce Tumor-Specific T Cell Chemorepulsion and Escape from Immune Control," J Immunol, 2006, 176:2902-2914.

Peng et al., "Molecular basis for the antagonistic activity of an anti-CXCR4 antibody," mAbs, Jan. 2016, 8(1):163-175.

Extended European Search Report in European Appln. No. 18772116.2, dated Apr. 7, 2021, 12 pages.

Fearon et al., "The carcinoma-associated fibroblast expressing fibroblast activation protein and escape from immune surveillance," Cancer Immunology Research, Mar. 2014, 2(3):187-193.

Gupta et al., "Role of human papillomavirus in oral squamous cell carcinoma and oral potentially malignant disorders: a review of the literature," Indian J Dent., Jan. 2015, 6(2):91-98, 12 pages.

Mellman et al., "De-risking immunotherapy: report of a consensus workshop of the cancer immunotherapy consortium of the cancer research institute," Cancer Immunology Research, Mar. 2016, 4(4):279-288.

Meuris et al., "Symptomatic improvement in human papillomavirus-induced epithelial neoplasia by specific targeting of the CXCR4 chemokine receptor," Journal of Investigative Dermatology, Feb. 2016, 136(2):473-480.

Meuris et al., "The CXCL12/CXCR4 signaling pathway: a new susceptibility factor in human papillomavirus pathogenesis," PLOS Pathogens, Dec. 2016, 12:e1006039, 25 pages.

Montoya et al., "Type I interferons produced by dendritic cells promote their phenotypic and functional activation," Blood, May 2002, 99(9):3263-3271.

Uchida et al., "Blockade of CXCR4 in oral squamous cell carcinoma inhibits lymph node metastases," European Journal of Cancer, Feb. 2011, 47(3):452-459.

Wang et al., "Oncogenic roles and drug target of CXCR4/CXCL12 axis in lung cancer and cancer stem cell," Tumor Biology, Apr. 2016, 37(7):8515-8528, 14 pages.

Office Action in Japanese Appln. No. 2019-552530, dated Apr. 5, 2022, 19 pages (with English translation).

* cited by examiner

CXCR4/CXCR7 BLOCKADE AND TREATMENT OF HUMAN PAPILLOMA VIRUS-ASSOCIATED DISEASE

STATEMENT OF PRIORITY

This application is a 35 U.S.C. § 371 national phase application of PCT Application PCT/US2018/023689 filed Mar. 22, 2018, which claims the benefit of U.S. Provisional Application Ser. No. 62/475,497, filed Mar. 23, 2017, and U.S. Provisional Application Ser. No. 62/503,988, filed May 10, 2017, the entire contents of each of which are incorporated by reference herein.

FIELD OF THE INVENTION

The present invention relates to methods and compositions for treating human papilloma virus (HPV)-associated diseases, treating immune checkpoint blockade resistant diseases, and enhancing the immune response against an HPV-associated disease using an inhibitor of CXCL12 signaling.

BACKGROUND OF THE INVENTION

CXCL12, formerly known as stromal cell-derived factor-1 (SDF-1), is a cytokine that is the natural ligand for CXCR4 receptors as well as CXCR7 receptors. The CXCR4/CXCL12 and CXCR7/CXCL12 chemokine receptor/chemokine axis has been shown to be involved in the pathogenesis of a number of hematological and solid malignancies. CXCR4/CXCL12 and CXCR7/CXCL12 signaling provides an immunosuppressive barrier that blocks the immune system from attacking cancer cells through immune evasion mechanisms including the recruitment of myeloid suppressor cells, tumor-infiltrating macrophages, and immunosuppressive regulatory T cells to the tumor and the repulsion of anti-tumor antigen specific $CD8^+$ T cells from the intratumoral microenvironment.

HPV is associated with many diseases including common, plantar, flat, hand and anogenital warts as well as mouth, respiratory and laryngeal papillomas. HPV infection is also associated with cancer. HPV-induced cancer has multiple oncogenic features.

There is a need in the art for improved treatments for HPV-associated diseases that can overcome the immunosuppressive barrier provided by many tumors and lesions that are associated with HPV and enhance the ability of the immune system to recognize and attack the cells of such tumors and lesions.

SUMMARY OF THE INVENTION

The present invention is based, in part, on the development of methods for overcoming the immunosuppressive barrier produced by many HPV-associated tumors and lesions and enhancing the body's immune response against the tumor and/or lesion. In particular, an inhibitor of CXCL12 signaling to reduce the immunosuppressive barrier may enhance treatment efficacy and survival of subjects having HPV-associated diseases.

Accordingly, one aspect of the invention relates to a method of treating a HPV-associated disease in a subject in need thereof, comprising delivering to the subject a therapeutically effective amount of an inhibitor of CXCL12 signaling, thereby treating the HPV-associated disease.

Another aspect of the invention relates to a method for enhancing an immune response against a HPV-associated disease in a subject in need thereof, comprising delivering to the subject a therapeutically effective amount of an inhibitor of CXCL12 signaling, thereby enhancing the immune response against the HPV-associated disease.

A further aspect of the invention relates to a method of treating an immune checkpoint blockade resistant disease in a subject in need thereof, comprising delivering to the subject a therapeutically effective amount of an inhibitor of CXCL12 signaling, thereby treating the immune checkpoint blockade resistant disease.

A further aspect of the invention relates to a composition comprising an inhibitor of CXCL12 signaling and a vaccine for inducing an immune response against HPV in a subject.

An additional aspect of the invention relates to a kit of parts comprising a first container comprising an inhibitor of CXCL12 signaling and a second container comprising a vaccine for inducing an immune response against HPV in a subject.

Another aspect of the invention relates to an inhibitor of CXCL12 signaling for use in treating an HPV-associated disease.

A further aspect of the invention relates to an inhibitor of CXCL12 signaling for use in enhancing an immune response against an HPV-associated disease.

An additional aspect of the invention relates to the use of an inhibitor of CXCL12 signaling in the preparation of a medicament for treating an HPV-associated disease.

Another aspect of the invention relates to the use of an inhibitor of CXCL12 signaling in the preparation of a medicament for enhancing an immune response against an HPV-associated disease.

These and other aspects of the invention are set forth in more detail in the description of the invention below.

DETAILED DESCRIPTION OF THE INVENTION

Figure 1:
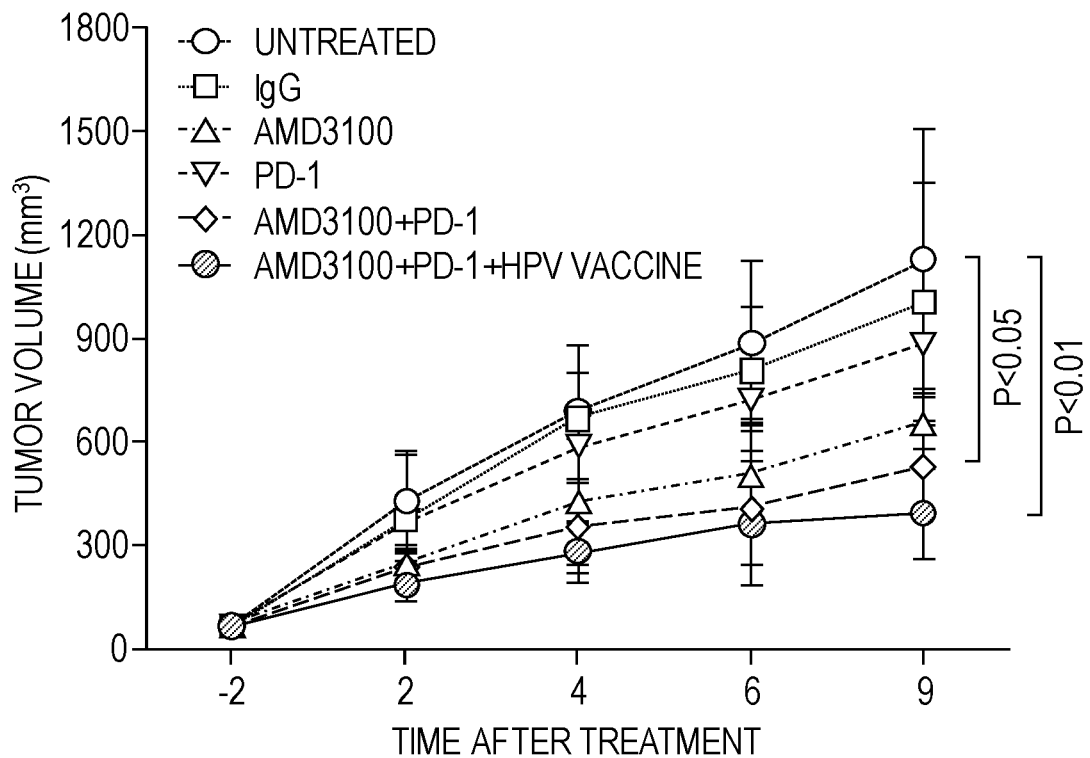
FIG. 1 shows tumor growth in mice following various treatments: AMD3100 (Δ), AMD3100 and PD-1 (◇), AMD3100, PD-1 and an HPV vaccine (⊘), PD-1 (▽), IgG (□) and untreated (○).

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±10%, ±5%, ±1%, ±0.5%, or even ±0.1% of the specified amount.

As used herein, the transitional phrase "consisting essentially of" (and grammatical variants) is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "modulate," "modulates," or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

The term "contact" or grammatical variations thereof as used with respect to a polypeptide and a receptor, refers to bringing the polypeptide and the receptor in sufficiently close proximity to each other for one to exert a biological effect on the other. In some embodiments, the term contact means binding of the polypeptide to the receptor.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

"Antibodies" as used herein include polyclonal, monoclonal, single chain, chimeric, humanized and human antibodies, prepared according to conventional methodology.

The terms "vaccine," "vaccination," and "immunization" are well-understood in the art, and are used interchangeably herein. For example, the terms vaccine, vaccination, or immunization can be understood to be a process or composition that increases a subject's immune reaction to an immunogen (e.g., by providing an active immune response), and therefore its ability to resist, overcome and/or recover from infection (i.e., a protective immune response).

"CXCL12 signaling" as used herein refers to the signaling pathways that involve binding of CXCL12 to its receptors, including CXCR4 and CXCR7.

"Human papilloma virus (HPV)-associated disease" as used herein refers to any disease correlated with an infection by HPV and/or a disease in which HPV can be detected and is believed to be a causal agent thereof. Over 150 distinct human papilloma viruses (HPVs) are recognized with each being associated with a specific set of clinical symptoms. The spectrum of diseases associated with HPV ranges from benign lesions to cancer.

A first aspect of the invention relates to a method of treating a HPV-associated disease in a subject in need thereof, comprising delivering to the subject a therapeutically effective amount of an inhibitor of CXCL12 signaling, thereby treating the HPV-associated disease.

Another aspect of the invention relates to a method for enhancing an immune response against a HPV-associated disease in a subject in need thereof, comprising delivering to the subject a therapeutically effective amount of an inhibitor of CXCL12 signaling, thereby enhancing the immune response against the HPV-associated disease. The term "enhancing an immune response against a human papilloma virus (HPV)-associated disease," as used herein, refers to increasing the ability of the immune system to recognize and/or attack tumors or lesion cells associated with HPV infection. Enhancements may include, without limitation, an increase in tumor- or lesion-specific cytotoxic lymphocytes, $CD8^+$ lymphocytes capable of delivering to the tumor or lesion Granzyme B, interferon, perforin, and/or Fas ligand, and/or a decrease in the co-location of T lymphocyte suppressor or regulatory cells and/or myeloid-derived suppressor cells, or any combination of the above.

Another aspect of the invention relates to a method of treating a patient having an immune checkpoint blockade resistant disease. "Immune checkpoint blockade resistant disease" as used herein refers to resistance to immune checkpoint inhibitor therapies that is present prior to administration of an immune checkpoint inhibitor or acquired after administration of an immune checkpoint inhibitor. Immune checkpoint blockade resistant diseases can include but are not limited to tumors that are unresponsive to a PD-1 inhibitor, unresponsive to a PD-L1 inhibitor, and/or unresponsive to a CTLA-4 inhibitor. Thus, some aspects the invention provide a method of treating a tumor unresponsive to a PD-1 inhibitor in a subject in need thereof, comprising delivering to the subject a therapeutically effective amount of an inhibitor of CXCL12 signaling, thereby treating the tumor that is unresponsive to a PD-1 inhibitor. In another aspect, the invention provides a method of treating a tumor unresponsive to a PD-L1 inhibitor in a subject in need thereof, comprising delivering to the subject a therapeutically effective amount of an inhibitor of CXCL12 signaling, thereby treating the tumor that is unresponsive to a PD-L1 inhibitor. A further aspect of the invention relates to a method of treating a tumor unresponsive to a CTLA-4 inhibitor in a subject in need thereof, comprising delivering to the subject a therapeutically effective amount of an inhibitor of CXCL12 signaling, thereby treating the tumor that is unresponsive to a CTLA-4 inhibitor. Any tumor that is or has become immune checkpoint blockade resistant may be treated as described herein.

The inhibitor of CXCL12 signaling may be any molecule that inhibits the CXCL12/CXCR4 and/or CXCL12/CXCR7 axis. The inhibitor may completely or partially inhibit signaling through the CXCL12/CXCR4 and/or CXCL12/CXCR7 axis when administered to a subject, e.g., providing at least about 30%, 40%, 50%, 60%, 70%, 80%, 90% or more inhibition of one or both receptor pathways. Inhibitors may include, without limitation, molecules that inhibit expression of CXCL12 or CXCR4 or CXCR7 (e.g., antisense or siRNA molecules), molecules that bind to CXCL12 or CXCR4 or CXCR7 and inhibit their function (e.g., antibodies or aptamers), molecules that inhibit dimerization of CXCL12 or CXCR4 or CXCR7, and antagonists of CXCR4 or CXCR7. In one embodiment, the inhibitor of CXCL12 signaling is a CXCR4 antagonist. The CXCR4 antagonist can be but is not limited to AMD3100, AMD11070 (also called AMD070), AMD12118, AMD11814, AMD13073, FAMD3465, C131, BKT140, CTCE-9908, KRH-2731, TC14012, KRH-3955, BMS-936564/MDX-1338, LY2510924, GSK812397, KRH-1636, T-20, T-22, T-140, TE-14011, T-14012, or TN14003, or an antibody that interferes with the dimerization of CXCR4. In one embodiment, the CXCR4 antagonist is AMD3100 (plerixafor). AMD3100 is described in U.S. Pat. No. 5,583,131, which is incorporated by reference herein in its entirety. In one embodiment, the inhibitor of CXCL12 signaling is a CXCR7 antagonist. The CXCR7 antagonist can be but is not limited to CCX771, CCX754, or an antibody that interferes with the dimerization of CXCR7. In certain embodiments, the inhibitor of CXCL12 signaling is not an antibody. In certain embodiments, the inhibitor of CXCL12 signaling is not a heparinoid. In certain embodiments, the inhibitor of CXCL12 signaling is not a peptide.

The methods of the invention may further comprise delivering to the subject one or more additional therapeutic agents, wherein the additional therapeutic agents may be chemotherapeutic agents and/or radiotherapeutic agents and/or immunotherapeutic agents. The methods of the invention may further comprise surgery to remove some or all of the tumor and/or post-surgery disease reduction.

In some aspects, an immunotherapeutic agent may be a vaccine for inducing an immune response against HPV in a subject, an immune checkpoint inhibitor, a natural killer cell, a T-cell, and/or an antibody specific for the HPV-associated disease.

A vaccine for inducing an immune response against HPV in a subject may be any vaccine directed to a human papilloma virus that is associated with a disease (e.g., an HPV vaccine) as disclosed herein. For example, an HPV vaccine useful with this invention may protect against one or more HPV types including, but not limited to, type 6, 11, 16, 18, 26, 31, 33, 35, 39, 42, 44, 45, 51, 52, 53, 56, 58, 59, 66, 68, 73, and/or 82. The HPV vaccine may be a live viral vaccine, live attenuated viral vaccine, or inactivated or killed viral vaccine. Example HPV vaccines useful with this invention include, but are not limited to, a vaccine that protects against HPV types 16 and 18, a vaccine that protects against HPV types 6, 11, 16, and 18, and/or a vaccine that protects against HPV types 6, 11, 16, 18, 31, 33, 45, 52, and 58 (see, e.g., CERVARIX®, GARDASIL®, GARDASIL 9®).

An immune checkpoint inhibitor may be any molecule that inhibits an immune checkpoint. Immune checkpoints are well known in the art and include, without limitation, PD-1, PD-L1, PD-L2, CTLA4, B7-H3, B7-H4, BTLA, IDO, KIR, LAG3, A2AR, TIM-3, and VISTA. In some embodiments, the inhibitor is an antibody against the immune checkpoint protein. In certain embodiments, the immune checkpoint inhibitor is an inhibitor of PD-1 or PD-L1, e.g., an antibody that specifically binds PD-1 or PD-L1. In some embodiments, the immune checkpoint inhibitor is nivolumab, pembrolizumab, ipilimumab, durvalumab, or atezolizumab. In one embodiment, the immune checkpoint inhibitor is nivolumab.

Inhibitors of CXCL12 signaling and immune checkpoint inhibitors are known in the art, for example, see U.S. Publication Nos. 2016/0235779, 2016/0304607, 2015/0352208, and 2015/0216843 and International Publication Nos. WO 2017/019767, WO 2017/009842, and WO 2016/201425.

The immunotherapeutic agent may be an anti-cancer vaccine (also called cancer vaccine). Anti-cancer vaccines are vaccines that either treat existing cancer or prevent development of a cancer by stimulating an immune reaction to kill the cancer cells. In one embodiment, the anti-cancer vaccine treats existing cancer.

The anti-cancer vaccine may be any such vaccine having a therapeutic effect on one or more types of cancer. Many anti-cancer vaccines are currently known in the art. Such vaccines include, without limitation, dasiprotimut-T, Sipuleucel-T, talimogene laherparepvec, HSPPC-96 complex (Vitespen), L-BLP25, gp100 melanoma vaccine, and any other vaccine that stimulates an immune response to cancer cells when administered to a patient. The anti-cancer vaccine may be an engineered molecule that targets cancer cells and delivers an immunostimulatory agent. For example, the vaccine may be a fusion protein comprising an antigen targeting portion (e.g., an antibody such as a scFv) and an immunostimulatory portion (e.g., a stress protein such as a heat shock protein). See, for example, U.S. Pat. Nos. 7,749,501 and 8,143,387 and International Publication No. WO 2017/156461.

Immunotherapeutic agents include natural killer cells, NK-92 cells, T cells, antibodies, and vaccines.

Natural killer (NK) cells are a class of lymphocytes that typically comprise approximately 10% of the lymphocytes in a human. NK cells provide an innate cellular immune response against tumor and infected (target) cells. NK cells, which are characterized as having a CD3⁻/CD56⁺ phenotype, display a variety of activating and inhibitory cell surface receptors. NK cell inhibitory receptors predominantly engage with major histocompatibility complex class I ("MHC-I") proteins on the surface of a normal cell to prevent NK cell activation. The MHC-I molecules define cells as "belonging" to a particular individual. It is thought that NK cells can be activated only by cells on which these "self MHC-I molecules" are missing or defective, such as is often the case for tumor or virus-infected cells.

NK cells are triggered to exert a cytotoxic effect directly against a target cell upon binding or ligation of an activating NK cell receptor to the corresponding ligand on the target cell. The cytotoxic effect is mediated by secretion of a variety of cytokines by the NK cells, which in turn stimulate and recruit other immune system agents to act against the target. Activated NK cells also lyse target cells via the secretion of the enzymes perforin and granzyme, stimulation of apoptosis-initiating receptors, and other mechanisms.

NK cells have been evaluated as an immunotherapeutic agent in the treatment of certain cancers. NK cells used for this purpose may be autologous or non-autologous (i.e., from a donor).

In one embodiment, the NK cells used in the compositions and methods herein are autologous NK cells. In one embodiment, the NK cells used in the compositions and methods herein are non-autologous NK cells.

In one embodiment, the NK cells used in the compositions and methods herein are modified NK cells. NK cells can be modified by insertion of genes or RNA into the cells such that the cells express one or more proteins that are not expressed by wild type NK cells. In one embodiment, the NK cells are modified to express a chimeric antigen receptor (CAR). In a preferred embodiment, the CAR is specific for the cancer being targeted by the method or composition.

Non-limiting examples of modified NK cells can be found, for example, in Glienke, et al. 2015, Advantages and applications of CAR-expressing natural killer cells, Frontiers in Pharmacol. 6, article 21; PCT Patent Pub. Nos. WO 2013154760 and WO 2014055668; each of which is incorporated herein by reference in its entirety.

The NK-92 cell line was discovered in the blood of a subject suffering from a non-Hodgkin's lymphoma. NK-92 cells lack the major inhibitory receptors that are displayed by normal NK cells, but retain a majority of the activating receptors. NK-92 cells are cytotoxic to a significantly broader spectrum of tumor and infected cell types than are NK cells and often exhibit higher levels of cytotoxicity toward these targets. NK-92 cells do not, however, attack normal cells, nor do they elicit an immune rejection response. In addition, NK-92 cells can be readily and stably grown and maintained in continuous cell culture and, thus, can be prepared in large quantities under c-GMP compliant quality control. This combination of characteristics has resulted in NK-92 being entered into presently on-going clinical trials for the treatment of multiple types of cancers.

NK-92 cells used in the compositions and methods described herein may be wild type (i.e., unmodified) NK-92 cells or modified NK-92 cells. NK-92 cells can be modified by insertion of genes or RNA into the cells such that the cells express one or more proteins that are not expressed by wild type NK-92 cells. In one embodiment, NK-92 cells are modified to express a chimeric antigen receptor (CAR) on the cell surface. In one embodiment, the CAR is specific for the cancer being targeted by the method or composition. In one embodiment, NK-92 cells are modified to express an Fc receptor on the cell surface. In one embodiment, the NK-92 cell expressing the Fc receptor can mediate antibody-dependent cell-mediated cytotoxicity (ADCC). In one embodiment, the Fc receptor is CD 16. In one embodiment, NK-92 cells are modified to express a cytokine (e.g., IL-2).

In one embodiment, the modified NK-92 cell is administered in combination with an antibody specific for the cancer to be treated. In one emboditnent, the modified NK-92 cell administered in combination with the antibody is competent to mediate ADCC.

Non-limiting examples of modified NK-92 cells are described, for example, in U.S. Pat. Nos. 7,618,817 and 8,034,332; and U.S. Patent Pub. Nos. 2002/0068044 and 2008/0247990, each of which is incorporated herein by reference in its entirety. Non-limiting examples of CAR-modified NK-92 cells can be found, for example, in Glienke, et al. 2015, Advantages and applications of CAR-expressing natural killer cells, Frontiers in Pharmacol. 6, article 21; which is incorporated herein by reference in its entirety.

T cells are lymphocytes having T-cell receptors in the cell surface. T cells play a central role in cell-mediated immunity by tailoring the body's immune response to specific pathogens. T cells, especially modified T cells, have shown promise in reducing or eliminating tumors in clinical trials. Generally, such T cells are modified and/or undergo adoptive cell transfer (ACT). ACT and variants thereof are well known in the art. See, for example, U.S. Pat. Nos. 8,383,099 and 8,034,334, which are incorporated herein by reference in their entireties.

U.S. Patent App. Pub. Nos. 2014/0065096 and 2012/0321666, incorporated herein by reference in their entireties, describe methods and compositions for T cell or NK cell treatment of cancer. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 2006/0121005, each of which is incorporated herein by reference in its entirety.

In one embodiment, the T cells used in the compositions and methods herein are autologous T cells (i.e., derived from the patient). In one embodiment, the T cells used in the compositions and methods herein are non-autologous (heterologous; e.g., from a donor or cell line) T cells. In one embodiment, the T cell is a cell line derived from T cell(s) or cancerous/transformed T cell(s).

In one embodiment, the T cell used in the methods and compositions described herein is a modified T cell. In one embodiment, the T cell is modified to express a CAR on the surface of the T cell. In one embodiment, the CAR is specific for the cancer being targeted by the method or composition. In one embodiment, the T cell is modified to express a cell surface protein or cytokine. Exemplary, non-limiting examples of modified T cells are described in U.S. Pat. No. 8,906,682; PCT Patent Pub. Nos. WO 2013154760 and WO 2014055668; each of which is incorporated herein by reference in its entirety.

In one embodiment, the T cell is a T cell line. Exemplary T cell lines include T-ALL cell lines, as described in U.S. Pat. No. 5,272,082, which is incorporated herein by reference in its entirety.

Immunotherapy also refers to treatment with anti-tumor antibodies. That is, antibodies specific for a particular type of cancer (e.g., a cell surface protein expressed by the target cancer cells) can be administered to a patient having cancer. The antibodies may be monoclonal antibodies, polyclonal antibodies, chimeric antibodies, antibody fragments, human antibodies, humanized antibodies, or non-human antibodies (e.g., murine, goat, primate, etc.). The therapeutic antibody may be specific for any tumor-specific or tumor-associated antigen. See, e.g., Scott et al., Cancer Immunity 2012, 12: 14, which is incorporated herein by reference in its entirety.

In one embodiment, the immunotherapy agent is an anti-cancer antibody. Non-limiting examples include trastuzumab (HERCEPTIN®), bevacizumab (AVASTIN®), cetuximab (ERBITUX®), panitumumab (VECTIBIX®), ipilimumab (YERVOY®), rituximab (RITUXAN®), alemtuzumab (CAMPATH®), ofatumumab (ARZERRA®), gemtuzumab ozogamicin (MYLOTARG®), brentuximab vedotin (ADCETRIS®), $^{90}$Y-ibritumomab tiuxetan (ZEVALIN®), and $^{131}$I-tositumomab (BEXXAR®).

Doses and administration protocols for immunotherapeutic drugs are well-known in the art. The skilled clinician can readily determine the proper dosing regimen to be used, based on factors including the immunotherapeutic agent(s) administered, type of cancer being treated, stage of the cancer, age and condition of the patient, patient size, location of the tumor, and the like. In some embodiments, immunotherapeutic agents may be administered at doses and schedules known in the art to be effective. In some embodiments, when combined with the methods of the present invention, immunotherapeutic agents may be administered at lower doses and/or with less frequency than typically used.

The chemotherapeutic agent may be any agent having a therapeutic effect on one or more types of cancer. Many chemotherapeutic agents are currently known in the art. Types of chemotherapy drugs include, by way of non-limiting example, alkylating agents, antimetabolites, anti-tumor antibiotics, topoisomerase inhibitors, mitotic inhibitors, corticosteroids, and the like.

Non-limiting examples of chemotherapeutic drugs include: nitrogen mustards, such as mechlorethamine (nitrogen mustard), chlorambucil, cyclophosphamide (CYTOXAN®), ifosfamide, and melphalan); nitrosoureas, such as streptozocin, carmustine (BCNU), and lomustine; alkyl sulfonates, such as busulfan; triazines, such as dacarbazine (DTIC) and temozolomide (TEMODAR®); ethylenimines, such as thiotepa and altretamine (hexamethylmelamine); platinum drugs, such as cisplatin, carboplatin, and oxalaplatin; 5-fluorouracil (5-FU); 6-mercaptopurine (6-MP); capecitabine (XELODA®); cytarabine (ARA-C®); floxuridine; fludarabine; gemcitabine (GEMZAR®); hydroxyurea; methotrexate; pemetrexed (ALIMTA®); anthracyclines, such as daunorubicin, doxorubicin (ADRIAMYCIN®), epirubicin, idarubicin; actinomycin-D; bleomycin; mitomycin-C; mitoxantrone; topotecan; irinotecan (CPT-11); etoposide (VP-16); teniposide; mitoxantrone; taxanes: paclitaxel (TAXOL®) and docetaxel (TAXOTERE®); epothilones: ixabepilone (IXEMPRA®); vinca alkaloids: vinblastine (VELBAN®), vincristine (ONCOVIN®), and vinorelbine (NAVELBINE®); estramustine (EMCYT®); prednisone; methylprednisolone (SOLUMEDROL®); dexamethasone (DECADRON®); L-asparaginase; and bortezomib (VELCADE®).

Doses and administration protocols for chemotherapeutic drugs are well-known in the art. The skilled clinician can readily determine the proper dosing regimen to be used, based on factors including the chemotherapeutic agent(s) administered, type of cancer being treated, stage of the cancer, age and condition of the patient, patient size, location of the tumor, and the like. In some embodiments, chemotherapeutic agents may be administered at doses and schedules known in the art to be effective. In some embodiments, when combined with the methods of the present invention, chemotherapeutic agents may be administered at lower doses and/or with less frequency than typically used.

The radiotherapeutic agent may be any such agent having a therapeutic effect on one or more types of cancer. Many radiotherapeutic agents are currently known in the art. Types of radiotherapeutic drugs include, by way of non-limiting example, X-rays, gamma rays, and charged particles. In one embodiment, the radiotherapeutic agent is delivered by a machine outside of the body (external-beam radiation therapy). In one embodiment, the radiotherapeutic agent is placed in the body near the tumor/cancer cells (brachytherapy) or is a systemic radiation therapy.

External-beam radiation therapy may be administered by any means. Exemplary, non-limiting types of external-beam radiation therapy include linear accelerator-administered radiation therapy, 3-dimensional conformal radiation therapy (3D-CRT), intensity-modulated radiation therapy (IMRT), image-guided radiation therapy (IGRT), tomotherapy, stereotactic radiosurgery, photon therapy, stereotactic body radiation therapy, proton beam therapy, and electron beam therapy.

Internal radiation therapy (brachytherapy) may be by any technique or agent. Exemplary, non-limiting types of internal radiation therapy include any radioactive agents that can be placed proximal to or within the tumor, such as radium-226 (Ra-226), cobalt-60 (Co-60), cesium-137 (Cs-137), cesium-131, iridium-192 (Ir-192), gold-198 (Au-198), iodine-125 (I-125), palladium-103, yttrium-90, etc. Such agents may be administered by seeds, needles, or any other route of administration, and may be temporary or permanent.

Systemic radiation therapy may be by any technique or agent. Exemplary, non-limiting types of systemic radiation therapy include radioactive iodine, ibritumomab tiuxetan (ZEVALIN®), tositumomab and iodine-131 tositumomab (BEXXAR®), samarium-153-lexidronam (QUADRAMET®), strontium-89 chloride (Metastron®), metaiodobenzylguanidine, lutetium-177, yttrium-90, strontium-89, and the like.

In one embodiment, a radiosensitizing agent is also administered to the patient. Radiosensitizing agents increase the damaging effect of radiation on cancer cells.

Doses and administration protocols for radiotherapy agents are well-known in the art. The skilled clinician can readily determine the proper dosing regimen to be used, based on factors including the agent(s) administered, type of cancer being treated, stage of the cancer, location of the tumor, age and condition of the patient, patient size, and the like. In some embodiments, radiotherapeutic agents may be administered at doses and schedules known in the art to be effective. In some embodiments, when combined with the methods of the present invention, radiotherapeutic agents may be administered at lower doses and/or with less frequency than typically used.

The inhibitor of CXCL12 signaling and the optional additional therapeutic agent may be delivered to the subject in any manner or pattern that is effective. In some embodiments, the inhibitor of CXCL12 signaling and additional therapeutic agent are delivered to the subject in the same composition. In other embodiments, the inhibitor of CXCL12 signaling and the additional therapeutic agent are delivered to the subject in separate compositions. The two agents may be delivered to the subject simultaneously. The two agents may be delivered to the subject sequentially and the sequence may be repeated as necessary, e.g., repeated 1, 2, 3, 4, 5, 6, 7, 8, 9, or 10 time or more.

In certain embodiments, the two agents may be delivered in the same pattern and/or schedule. In other embodiments, the two agents may be delivered in a different pattern and/or schedule. In some embodiments, the additional therapeutic agent may be an immunotherapeutic agent that may be administered to the subject for a sufficient amount of time to stimulate the immune system and then stopped. For example, the immunotherapeutic agent may be administered for just a few doses, e.g., 10 doses or less, e.g., 10, 9, 8, 7, 6, 5, 4, 3, 2, or 1 dose, in a periodic fashion, e.g., once every week, 2 weeks, 3 weeks, 4 weeks, 5 weeks, 6 weeks, or more. In some embodiments, the inhibitor of CXCL12 signaling may be administered for a longer period of time than the additional therapeutic agent, e.g., until the HPV-associated disease has been successfully treated. The inhibitor of CXCL12 signaling also may be administered more frequently than the additional therapeutic agent, e.g., once every 3 hours, 4 hours, 6 hours, 12 hours, day, 2 days, 3 days, 4 days, 5, days, 6, days, week, or more.

The HPV-associated disease to be treated may be any HPV-associated disease for which the methods of the invention are effective. In some embodiments, the HPV-associated disease is a HPV positive tumor and/or lesion. In some embodiments, the HPV positive tumor and/or lesion can include, but is not limited to, cervical intraepithelial neoplasia 1, cervical intraepithelial neoplasia 2, cervical intraepithelial neoplasia 3, cervical cancer (in situ and/or invasive), head and neck cancer (e.g., squamous cell carcinoma), HPV papillomatosis, anal papillomatosis, anal cancer, vaginal cancer, vulvar cancer, and/or penile cancer. In some embodiments, the cervical cancer may be adenocarcinoma of the cervix and/or squamous cell carcinoma of the cervix. In some embodiments, the HPV papillomatosis may be recurrent respiratory papillomatosis (RRP) and/or laryngeal papillomatosis.

In one embodiment, the inhibitors of the invention are administered directly to a subject. Generally, the inhibitors of the invention will be suspended in a pharmaceutically-acceptable carrier (e.g., physiological saline) and administered orally or by intravenous infusion, or administered subcutaneously, intramuscularly, intrathecally, intraperitoneally, intrarectally, intravaginally, intranasally, intragastrically, intratracheally, or intrapulmonarily. In another embodiment, the intratracheal or intrapulmonary delivery can be accomplished using a standard nebulizer, jet nebulizer, wire mesh nebulizer, dry powder inhaler, or metered dose inhaler. They can be delivered directly to the site of the disease or disorder, such as the skin, the cervix, the head, the neck, or directly into a tumor or lesion.

In one embodiment, the inhibitors are administered proximal to (e.g., near or within the same body cavity as) the tumor, e.g., into the peritoneal or pleural cavity, or topically, e.g., to the skin or a mucosal surface, e.g., to the cervix. In one embodiment, the inhibitors are administered directly into the tumor or into a blood vessel feeding the tumor. In one embodiment, the inhibitors are administered systemically. In a further embodiment, the inhibitors are administered by microcatheter, or an implanted device, or an implanted dosage form.

In one embodiment, the inhibitors are administered in a continuous manner for a defined period. In another embodiment, the inhibitors are administered in a pulsatile manner. For example, the inhibitors may be administered intermittently over a period of time. The agents may be administered in the same or different patterns and for the same or different lengths of time.

The dosage required depends on the choice of the route of administration; the nature of the formulation; the nature of the patient's illness; the subject's size, weight, surface area, age, and sex; other drugs being administered; and the judgment of the attending physician. Wide variations in the needed dosage are to be expected in view of the variety of molecules available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the inhibitors in a suitable delivery vehicle (e.g., polymeric microparticles, slow release polymeric gels, or implantable devices) may increase the efficiency of delivery, particularly for oral delivery or delivery into or nearby the location of a tumor, e.g., the peritoneal or pleural cavity.

Generally, the dose of each of the inhibitors of the present invention is from about 0.01 mg/kg body weight per day to about 100 mg/kg per day, e.g., about 0.1 mg/kg body weight per day to about 50 mg/kg per day, inclusive of all values and ranges therebetween, including endpoints. In one embodiment, the dose is from about 0.1 mg/kg to about 50 mg/kg per day. In one embodiment, the dose is from about 0.1 mg/kg to about 40 mg/kg per day. In one embodiment, the dose is from about 0.1 mg/kg to about 30 mg/kg per day. In one embodiment, the dose is from about 0.1 mg/kg to about 20 mg/kg per day. In one embodiment, the dose does not exceed about 50 mg per day.

In one embodiment, the dose is from about 0.5 mg/kg per week to about 350 mg/kg per week, inclusive of all values and ranges therebetween, including endpoints. In one embodiment, the dose is about 0.5 mg/kg per week. In one embodiment, the dose is about 1 mg/kg per week. In one embodiment, the dose is about 2 mg/kg per week. In one embodiment, the dose is about 5 mg/kg per week. In one embodiment, the dose is about 10 mg/kg per week. In one embodiment, the dose is about 20 mg/kg per week. In one embodiment, the dose is about 30 mg/kg per week. In one embodiment, the dose is about 40 mg/kg per week. In one embodiment, the dose is about 50 mg/kg per week. In one embodiment, the dose is about 60 mg/kg per week. In one embodiment, the dose is about 70 mg/kg per week. In one embodiment, the dose is about 80 mg/kg per week. In one embodiment, the dose is about 90 mg/kg per week. In one embodiment, the dose is about 100 mg/kg per week. In one embodiment, the dose is about 110 mg/kg per week. In one embodiment, the dose is about 120 mg/kg per week. In one embodiment, the dose is about 130 mg/kg per week. In one embodiment, the dose is about 140 mg/kg per week. In one embodiment, the dose is about 150 mg/kg per week. In one embodiment, the dose is about 160 mg/kg per week. In one embodiment, the dose is about 170 mg/kg per week. In one embodiment, the dose is about 180 mg/kg per week. In one embodiment, the dose is about 190 mg/kg per week. In one embodiment, the dose is about 200 mg/kg per week. In one embodiment, the dose is about 210 mg/kg per week. In one embodiment, the dose about 220 mg/kg per week. In one embodiment, the dose is about 230 mg/kg per week. In one embodiment, the dose is about 240 mg/kg per week. In one embodiment, the dose is about 250 mg/kg per week. In one embodiment, the dose is about 260 mg/kg per week. In one embodiment, the dose is about 270 mg/kg per week. In one embodiment, the dose is about 280 mg/kg per week. In one embodiment, the dose is about 290 mg/kg per week. In one embodiment, the dose is about 300 mg/kg per week. In one embodiment, the dose is about 310 mg/kg per week. In one embodiment, the dose is about 320 mg/kg per week. In one embodiment, the dose is about 330 mg/kg per week. In one embodiment, the dose is about 340 mg/kg per week. In one embodiment, the dose is about 350 mg/kg per week.

In one aspect of the invention, administration of one or both of the inhibitors is pulsatile. In one embodiment, an amount of one or both of the inhibitors is administered every 1 hour to every 24 hours, for example every 1 hour, 2 hours, 3 hours, 4 hours, 5 hours, 6 hours, 7 hours, 8 hours, 9 hours, 10 hours, 11 hours, 12 hours, 13 hours, 14 hours 15 hours, 16 hours, 17 hours, 18 hours, 19 hours, 20 hours, 21 hours, 22 hours, 23 hours, or 24 hours. In one embodiment, an amount of one or both of the inhibitors is administered every 1 day, 2 days, 3 days, 4 days, 5 days, 6 days, 7 days, 8 days, 9 days, or 10 days.

In certain embodiments, the administration of the inhibitors may be of indefinite duration, to be determined by the managing physician, and only terminated when the disease is judged to be either cured or in remission.

In one embodiment, when the inhibitor of CXCL12 signaling is provided with an additional therapeutic agent, the administration of the inhibitor of CXCL12 signaling and the additional therapeutic agent is alternated. In one embodiment, administration of the inhibitor of CXCL12 signaling and the additional therapeutic agent is alternated until the condition of the patient improves. Improvement includes, without limitation, reduction in size of the tumor and/or metastases thereof, elimination of the tumor and/or metastases thereof, remission of the cancer, and/or attenuation of at least one symptom of the cancer.

According to certain embodiments, the inhibitors can be targeted to specific cells or tissues in vivo. Targeting delivery vehicles, including liposomes and targeted systems are known in the art. For example, a liposome or particle can be directed to a particular target cell or tissue, e.g., a cancer cell, tumor, or lesion, by using a targeting agent, such as an antibody, soluble receptor or ligand, incorporated with the liposome or particle, to target a particular cell or tissue to which the targeting molecule can bind. Targeting liposomes are described, for example, in Ho et al., *Biochemistry* 25:5500 (1986); Ho et al., *J. Biol. Chem.* 262:13979 (1987); Ho et al., *J. Biol. Chem.* 262:13973 (1987); and U.S. Pat. No. 4,957,735 to Huang et al., each of which is incorporated herein by reference in its entirety).

In some embodiments, the inhibitor of CXCL12 signaling and the additional therapeutic agent (e.g., immunotherapeutic agent (e.g., HPV vaccine, immune checkpoint inhibitor, anti-cancer vaccine); chemotherapeutic agent; radiotherapeutic agent) may be administered by the same route. In other embodiments, the inhibitor of CXCL12 signaling and the additional therapeutic agent may be administered by different routes, e.g., by the route most suitable for each agent. For example, the additional therapeutic agent may be administered systemically (e.g., intravenously) and the inhibitor of CXCL12 signaling may be administered locally (e.g., directly into a tumor or into a body cavity containing the tumor) or the inhibitor of CXCL12 signaling may be administered systemically and the additional therapeutic agent may be administered locally. In some embodiments, the immune checkpoint inhibitor may be administered by intravenous infusion and the inhibitor of CXCL12 signaling may be administered by subcutaneous injection or by subcutaneous pump to a local tumor site or for systemic delivery.

As a further aspect, the invention provides pharmaceutical formulations and methods of administering the same to achieve any of the therapeutic effects (e.g., treatment of HPV-associated disease) discussed above. The pharmaceutical formulation may comprise any of the reagents discussed above in a pharmaceutically acceptable carrier.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The agents of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the agent (including the physiologically acceptable salts thereof) is typically admixed with, inter alia, an acceptable carrier. The carrier can be a solid or a liquid, or both, and may be formulated with the agent as a unit-dose formulation, for example, a tablet, which can contain from 0.01 or 0.5% to 95% or 99% by weight of the agent. One or more agents can be incorporated in the formulations of the invention, which can be prepared by any of the well-known techniques of pharmacy.

A further aspect of the invention is a method of treating subjects in vivo, comprising administering to a subject a pharmaceutical composition comprising the inhibitors of the invention in a pharmaceutically acceptable carrier, wherein the pharmaceutical composition is administered in a therapeutically effective amount. Administration of the inhibitors of the present invention to a human subject or an animal in need thereof can be by any means known in the art for administering compounds.

The formulations of the invention include those suitable for oral, rectal, perianal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular treatment being administered.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the inhibitors can be administered in solid dosage forms, such as capsules, tablets, and powders, or in liquid dosage forms, such as elixirs, syrups, and suspensions Inhibitors can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the inhibitors in a flavored base, usually sucrose and acacia or tragacanth; and pastilles comprising the inhibitors in an inert base such as gelatin and glycerin or sucrose and acacia.

Formulations of the present invention suitable for parenteral administration comprise sterile aqueous and non-aqueous injection solutions of the inhibitors, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising inhibitors of the invention, in a unit dosage form in a sealed container. The inhibitor of CXCL12 signaling and/or the additional therapeutic agent are provided in the form of a lyophilizate which is capable of being reconstituted with a suitable pharmaceutically acceptable carrier to form a liquid composition suitable for injection thereof into a subject. The unit dosage form typically comprises from about 0.01 mg to about 10 grams of the inhibitor of CXCL12 signaling and/or the additional therapeutic agent. When the inhibitor of CXCL12 signaling and/or the additional therapeutic agent are substantially water-insoluble, a sufficient amount of emulsifying agent which is pharmaceutically acceptable can be employed in sufficient quantity to emulsify the inhibitor and/or agent in an aqueous carrier. One such useful emulsifying agent is phosphatidyl choline.

Formulations suitable for rectal administration are preferably presented as unit dose suppositories. These can be prepared by admixing the inhibitor and/or agent with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the polypeptides. Suitable formulations comprise citrate or bis/tris buffer (pH 6) or ethanol/water and contain from 0.1 to 0.2M of the compound.

The inhibitor and/or agent can alternatively be formulated for nasal administration or otherwise administered to the lungs of a subject by any suitable means, e.g., administered by an aerosol suspension of respirable particles comprising the inhibitor and/or agent, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract,* Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the inhibitor and/or agent can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the inhibitor and/or agent can likewise be produced with any solid particulate medicament aerosol generator, by techniques known in the pharmaceutical art.

Alternatively, one can administer the inhibitor and/or agent in a local rather than systemic manner, for example, in a depot or sustained-release formulation.

Further, the present invention provides liposomal formulations of the inhibitor and/or agent disclosed herein and salts thereof. The technology for forming liposomal suspensions is well known in the art. When the inhibitor and/or agent or salt thereof is an aqueous-soluble salt, using conventional liposome technology, the same can be incorporated into lipid vesicles. In such an instance, due to the water solubility of the inhibitor/agent or salt, the inhibitor/agent or salt thereof will be substantially entrained within the hydrophilic center or core of the liposomes. The lipid layer employed can be of any conventional composition and can either contain cholesterol or can be cholesterol-free. When the inhibitor/agent or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the inhibitor and/or agent disclosed herein or salts thereof, can be lyophilized to produce a lyophilizate which can be reconstituted with a pharmaceutically acceptable carrier, such as water, to regenerate a liposomal suspension.

In the case of water-insoluble inhibitors, a pharmaceutical composition can be prepared containing the water-insoluble inhibitors, such as for example, in an aqueous base emulsion. In such an instance, the composition will contain a sufficient amount of pharmaceutically acceptable emulsifying agent to emulsify the desired amount of the inhibitors. Particularly useful emulsifying agents include phosphatidyl cholines and lecithin.

In particular embodiments, the inhibitor of CXCL12 signaling and/or additional therapeutic agent may be administered to the subject in a therapeutically effective amount, as that term is defined above. Dosages of pharmaceutically active inhibitors can be determined by methods known in the art, see, e.g., *Remington's Pharmaceutical Sciences* (Maack Publishing Co., Easton, Pa.). The therapeutically effective dosage of any specific inhibitor or other therapeutic agent will vary somewhat from inhibitor to inhibitor, agent to agent, and patient to patient, and will depend upon the condition of the patient and the route of delivery. As a general proposition, a dosage from about 0.1 to about 50 mg/kg will have therapeutic efficacy, with all weights being calculated based upon the weight of the inhibitor/agent, including the cases where a salt is employed. Toxicity concerns at the higher level can restrict intravenous dosages to a lower level such as up to about 10 mg/kg, with all weights being calculated based upon the weight of the inhibitor, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmol/kg and to 33 µmol/kg of the inhibitor of CXCL12 signaling and/or additional therapeutic agent for intravenous or oral administration, respectively. In some aspects, a dosage of an HPV vaccine may comprise about 10-80 µg (e.g., about 10, 20, 30, 40, 50, 60, 70, 80 µg, and any range or value therein) HPV protein for intramuscular injection.

In particular embodiments of the invention, more than one administration (e.g., two, three, four, or more administrations) can be employed over a variety of time intervals (e.g., hourly, daily, weekly, monthly, etc.) to achieve therapeutic effects. Thus, for example, an HPV vaccine may be administered in three doses at 0 months, 2 months and 6 months or at 0 months, 1 month and 6 months, or in two doses at 0 months and 6-12 months.

Other delivery systems can include time-release, delayed release or sustained release delivery systems. Such systems can avoid repeated administrations of the inhibitor of CXCL12 signaling and/or additional therapeutic agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like.

In one embodiment, the inhibitor and/or agent may be administered in a time-release, delayed release or sustained release delivery system. In one embodiment, the time-release, delayed release or sustained release delivery system comprising the inhibitor and/or agent may be inserted directly into the tumor. In one embodiment, the time-release, delayed release or sustained release delivery system comprising the inhibitor and/or agent may be implanted in the patient proximal to the tumor. Additional implantable formulations are described, for example, in U.S. Patent App. Pub. No. 2008/0300165, which is incorporated herein by reference in its entirety.

In addition, important embodiments of the invention include pump-based hardware delivery systems, some of which are adapted for implantation. Such implantable pumps include controlled-release microchips. A preferred controlled-release microchip is described in Santini, J T Jr. et al., Nature, 1999, 397:335-338, the contents of which are expressly incorporated herein by reference.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults.

Another aspect of the invention relates to a composition comprising an inhibitor of CXCL12 signaling and a vaccine for inducing an immune response against HPV (HPV vaccine) in a subject.

A further aspect of the invention relates to a kit of parts comprising a first container comprising an inhibitor of CXCL12 signaling and a second container comprising an HPV vaccine.

The inhibitor of CXCL12 signaling and the HPV vaccine in the composition or the kit of parts may be any of the agents described above.

The container may be, without limitation, a vial containing a single dose or multiple doses of the inhibitor or vaccine or a prefilled syringe containing the inhibitor or vaccine.

In one embodiment, the composition or kit of parts further comprises instructions in a readable medium for dosing and/or administration of the inhibitor of CXCL12 signaling and the HPV vaccine. The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

The present invention is more particularly described in the following examples that are intended as illustrative only since numerous modifications and variations therein will be apparent to those skilled in the art.

EXAMPLES

The overall objective response rate of locally recurrent and/or metastatic (R/M) head and neck squamous cell carcinoma (HNSCC) patients to anti-PD1 monotherapy is 18%. While these response rates are promising, there is an opportunity to increase the clinical impact of pembrolizumab with novel combinatorial strategies. Immune checkpoint blockade therapy potentiates the activity of existing CD8$^+$ T cells and, ultimately, clinical efficacy can be limited by the number of infiltrating CD8$^+$ T cells within the tumor microenvironment. Head and neck cancer patients who failed anti-PD-1 monotherapy may have failed due to a paucity of CD8+ T cells present within the tumor microenvironment.

CXCL12 is a chemoattractant for CD8$^+$ T cells and our group has reported that high levels of CXCL12 paradoxically can elicit an immunosuppressive microenvironment with decreased CD8$^+$ T cell infiltration through increased binding of CXCR4 expressed on the T cells (resulting in chemorepulsion) and increased recruitment of immunosuppressive CD4$^+$FoxP3$^+$ T regulatory (Treg) cells (*J Immunol* 2006; 176:2902-2914; *Cancer Res* 2011 71(16):5522-34). It has been demonstrated that cervical cancer and HNSCCs, in particular human papillomavirus (HPV)-associated HNSCCs, over-express CXCL12 (*Am J Pathol* 2009, 175: 1525-35). The present study is directed to targeting the CXCL12:CXCR4 axis to determine if intratumoral CD8$^+$ T cell recruitment may be increased and, thus, increase the clinical response rates to anti-PD-1 therapy.

Plerixafor (AMD3100), a small molecule, is approved by the US Food and Drug Administration (FDA) for mobilizing hematopoietic stem cells from the bone marrow to the blood for transplantation in cancer and is a highly specific antagonist of CXCR4. Administration of AMD3100 can rapidly mobilize all major subsets of mature leukocytes into the blood. A phase I clinical trial demonstrated the safety of long-term, low-dose treatment with AMD3100 at a dose of 0.01-0.02 mg/kg (4-8% of the FDA-approved dose) administered subcutaneously twice daily for 6 months (*Blood* 2014; 123(15):2308-16).

Example 1

AMD3100 in Combination with Pembrolizumab

The combination of AMD3100 and a blocking anti-PD-1 antibody was evaluated in a preclinical head and neck tumor model that is resistant to anti-PD-1 monotherapy.

Methods. C57BL/6 mice were inoculated with 1×10$^5$ TC-1 tumor cells subcutaneously into the right flank. When tumors reached approximately 60-70 mm$^3$ in size, various treatments were initiated. The treatment groups (N=5) consisted of no treatment, administration of an isotype control IgG antibody (clone 2A3, BioXcell), anti-PD-1 monotherapy (clone 29F.1A12, BioXcell), AMD3100 monotherapy (catalog AB120718, AbCam), combination of AMD3100 and anti-PD-1 and combination of AMD3100, anti-PD-1, and an HPV vaccine (See, FIGS. 1, 2, 3, and 4).

The treatment regimen consisted of administration of 0.5 mg/mouse of anti-PD-1 antibody (clone 29F.1A12, BioXcell) or isotype control antibody (clone 2A3, BioXcell) every 5 days for a total of 3 treatments. Prior to each dose of antibody, the mice were treated with 3 mg/kg of AMD3100 (catalog AB120718, AbCam). In addition, a subset of mice were treated with a 1:1 ratio of 20 mcg of HPV E7 peptide vaccine and 20 mcg of poly I:C adjuvant in a total volume of 20 µl, which was administered intratumorally. The tumors were measured twice a week with calipers. When the tumor measured over 2 centimeters in any one direction, the animal was sacrificed according to IACUC policy.

Figure 2:
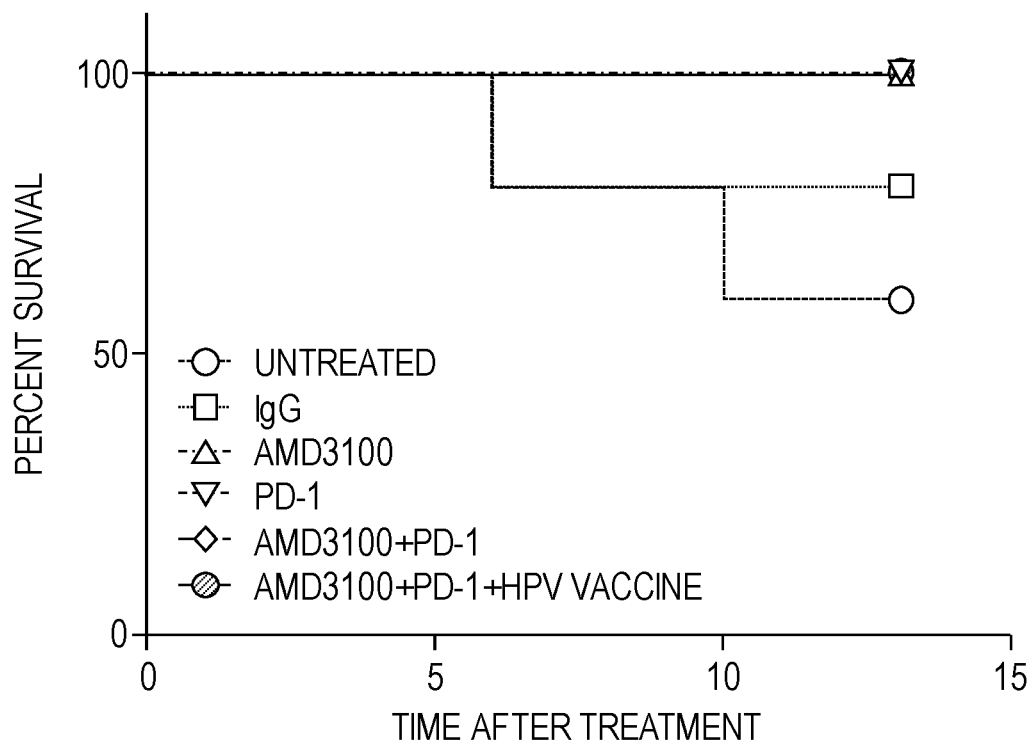
FIG. 2 shows the survival of mice treated with AMD3100 (Δ), AMD3100 and PD-1 (◇), AMD3100, PD-1 and an HPV vaccine (⊘), PD-1 (▽), IgG (□) and untreated (○). Survival of the mice after tumor inoculation is plotted for all of the different treatment groups. Survival differences were assessed by the Log-rank test. Survival of mice in treatment groups was assessed up to 15 days post treatment. Survival of mice with PD1 alone, AMD3100+PD1 or AMD3100+PD1+HPV all overlap with the survival curve for AMD3100 alone.
Figure 3:
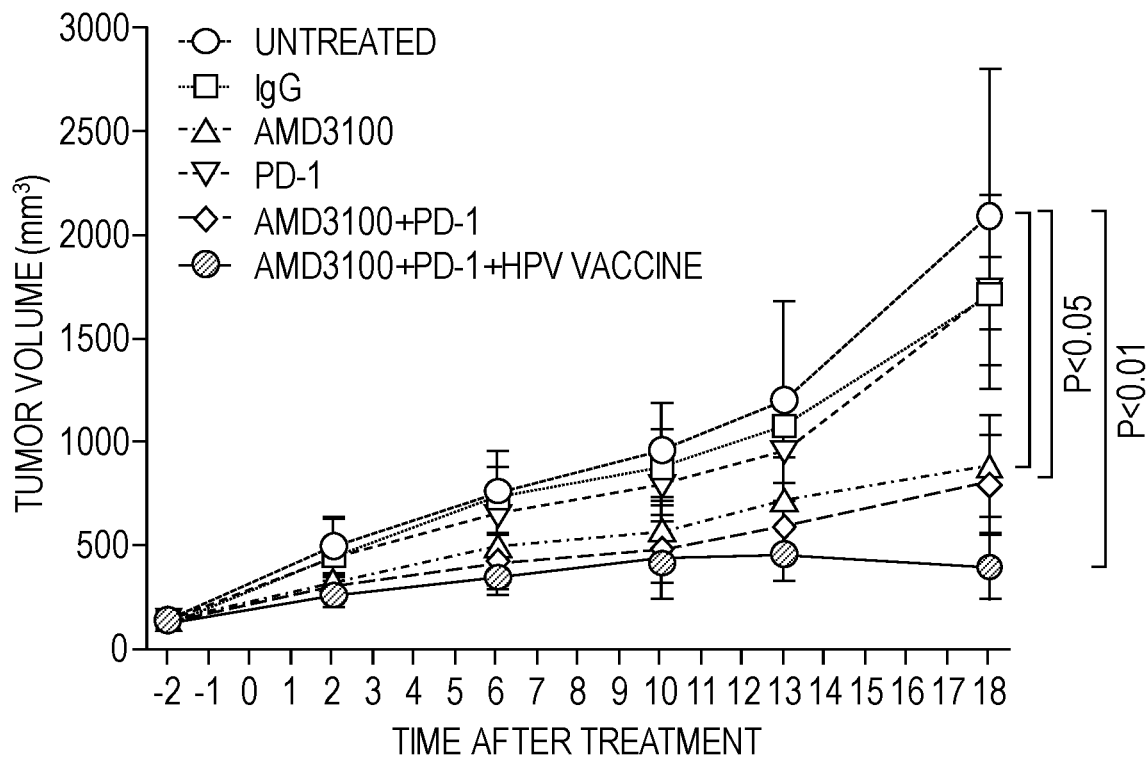
FIG. 3 shows tumor growth in mice following various treatments: AMD3100 (Δ), with AMD3100 and PD-1 (◇), AMD3100, PD-1 and an HPV vaccine (⊘), PD-1 (▽), IgG (□) and untreated (○). Tumor volume was measured through the caliper based assessment of two dimensions of the subcutaneous tumor at day −2 to 18 days post treatment initiation. Statistical tests (by ANOVA) were performed and are shown in the figure.
Figure 4:
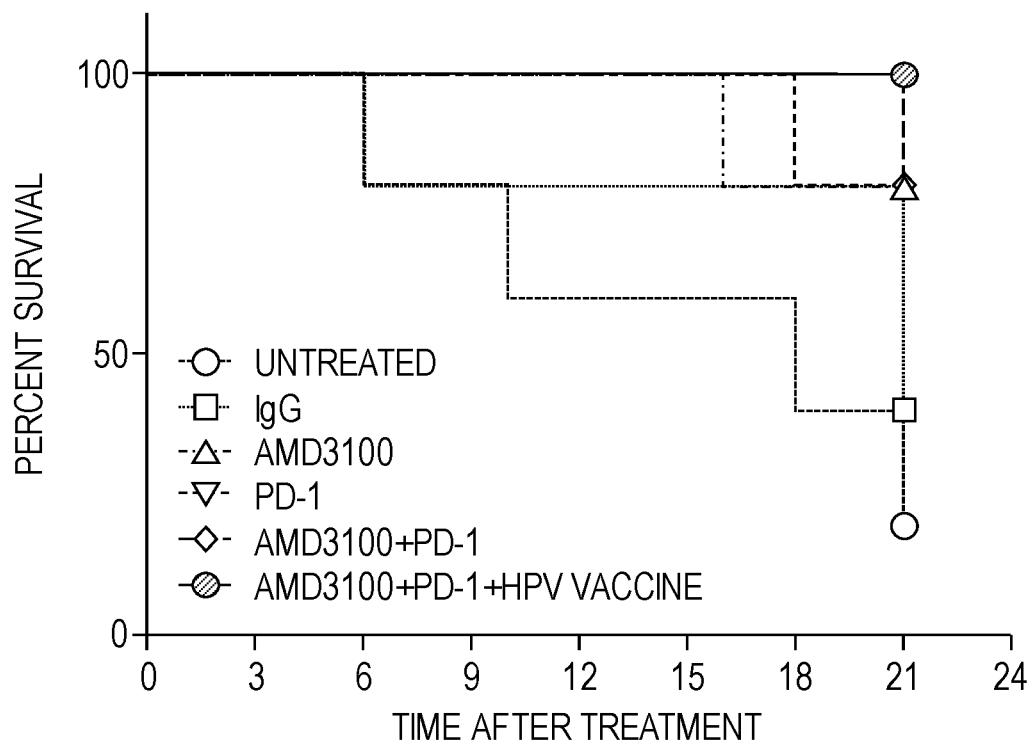
FIG. 4 shows the survival of mice treated with AMD3100 (Δ), AMD3100 and PD-1 (◇), AMD3100, PD-1 and an HPV vaccine (⊘), PD-1 (▽), IgG (□) and untreated (○). Survival of the mice after tumor inoculation is plotted for all of the different treatment groups. Survival differences were assessed by the Log-rank test. Survival of mice in treatment groups was assessed up to 21 days post treatment when the mice were all sacrificed.

We found that the combination of AMD3100, the combination of AMD3100 and anti-PD-1 and the combination of AMD3100, anti-PD-1 and an HPV vaccine resulted in an enhanced anti-tumor effect (FIG. 1, FIG. 3) with associated prolonged survival (FIG. 2, FIG. 4).

In an ovarian preclinical cancer model, we found that AMD3100 is able to increase CD8$^+$ T cells and decrease Treg infiltration that translated into an enhanced anti-tumor effect.

Based on our preliminary data, a phase II clinical trial is proposed in HNSCC patients who have progressed on anti-PD-1 monotherapy. Anti-PD-1 resistant HNSCC patients will be treated with the combination of AMD3100 and pembrolizumab with a safety run-in period, since these agents have never been administered in combination in humans.

Example 3

Study Design/Clinical Plan for a Phase II Clinical Trial for Treatment of Recurrent/Metastatic Head and Neck Cancer AMD3100 in combination with pembrolizumab will be administered to 41 adult male and female patients diagnosed with R/M HNSCC and who have progressed on anti-PD-1 monotherapy. Since these agents have never been administered in combination, we are proposing a safety run-in in 6 patients for which we will evaluate 2 doses of AMD3100. The first dose cohort will receive AMD3100 at a dose of 0.24 mg/kg SQ Day1, then 0.02 mg/kg every other day SQ for 6 weeks in combination with pembrolizumab 200 mg IV q3 weeks×2 cycles. The second dose cohort will receive AMD3100 at a dose of 0.24 mg/kg SQ Day1, then 0.02 mg/kg daily SQ for 6 weeks in combination with pembrolizumab 200 mg IV q3 weeks×2 cycles. Three patients will be entered into each dose, first into the every-other-day dosing, then 3 into the every-day dosing. If zero or one dose limiting toxicity (DLT) is observed through the first month after the second cycle in a dose, then that dose will be considered for the phase II portion. If there are 2 or more "DLTs" observed through the first month after the second cycle in the three patients in a dose, then further evaluation of the events will be performed prior to using that dose in the phase II portion. The dose with the least adverse event profile will be used in the phase II portion. In the safety run-in, all patients will also undergo a pre- and post-treatment biopsy at week 6 in which they will be evaluated for changes in the CD8/Treg ratio. If both doses of AMD3100 in combination with pembrolizumab are determined to be safe, then we will proceed with the dose that results in an increased CD8/Treg ratio within the tumor microenvironment. If both doses result in comparable changes in the CD8/Treg ratio, we will proceed with the less frequent dosing regimen of AMD3100 for the phase II trial.

In the phase II study, patients will be administered the combination of AMD3100 (at the dose determined to be safe in the run-in period) and pembrolizumab (e.g., 200 mg IV q3 weeks) for up to 24 months. Tumor assessments by CT or MRI imaging will be obtained every 8 weeks until first progression, death, or 24 months from study registration whichever occurs first. If protocol treatment is discontinued for reasons other than disease progression, tumor assessments are to continue every 2 months until first progression, death, or 24 months from study registration, whichever occurs first. After first progression, survival status will continue to be assessed every 8 weeks until 24 months from study registration or until death whichever occurs first. A tumor biopsy and peripheral blood will be collected on all patients pre-treatment and at week 8. Tumor infiltrating cytotoxic $CD8^+$ T cells and $CD4^+FoxP3^+$ Treg ratios will be determined by quantitative multi-spectral imaging (MSI).

No patients from the safety run-in will be included in the phase II portion as the safety run in consists of 2 cycles and in the phase II portion, cycles will continue for up to 2 years. For the phase II portion, a two-stage design (Simon Optimal) will be used to minimize the number of patients enrolled. If >22 evaluable patients (defined as those who are eligible and have begun protocol treatment) have disease which has responded out of a total of 41 evaluable patients (assuming that >3 of the first 19 evaluable patients entered in the first stage have disease which has responded), further study of the regimen will be considered. This design has 84% probability of declaring the regimen effective if the true response rate is 34%, and 10% probability if the true response rate is 18%.

Toxicity will be assessed using the NCI Common Toxicity Criteria for Adverse Events, version 4. A dose limiting toxicity (DLT) is defined in this study as any grade 3 adverse event(s) other than injection site reactions or any grade 4 adverse event(s), including injection site reactions, which occur in a subject through the first month after the second cycle. In addition, to be considered a DLT in this study the adverse event must be considered at least possibly related to study treatment.

Collateral Research. Peripheral blood and biopsies will be obtained pre- and on-treatment at week 8. With the pre- and on-treatment tumor biopsies, we will evaluate for changes at the transcriptional level using RNASeq, evaluate for changes in the $CD8^+$/Treg ratio, PD-1, PD-L1, CD4, FoxP3, NK, and MDSC infiltration using multi-spectral imaging and mass spectrometry, as well as evaluate for changes in PD-L1 protein expression via IHC. For a subset of samples, phenotypic and functional characterization of immune cells will be performed using multi-color flow cytometry and/or CyTOF.

The foregoing is illustrative of the present invention, and is not to be construed as limiting thereof. The invention is defined by the following claims, with equivalents of the claims to be included therein.

That which is claimed is:

1. A method of treating a human papilloma virus (HPV)-associated disease in a subject in need thereof, comprising delivering to the subject:
    (a) a therapeutically effective amount of AMD3100; and
    (b) an immune checkpoint PD-1 inhibitor, thereby treating the HPV-associated disease,
    wherein the HPV-associated disease is cervical cancer.

2. The method of claim 1, wherein the cervical cancer is cervical intraepithelial neoplasia 1, cervical intraepithelial neoplasia 2, cervical intraepithelial neoplasia 3, or cervical cancer (in situ and/or invasive).

3. The method of claim 2, wherein the cervical cancer is adenocarcinoma of the cervix and/or squamous cell carcinoma of the cervix.

4. The method of claim 1, further comprising delivering to the subject a vaccine for inducing an immune response against HPV in the subject.

5. The method of claim 1, further comprising delivering to the subject a natural killer cell or a T cell.

6. The method of claim 1, further comprising delivering to the subject an antibody specific for the HPV-associated disease.

7. The method of claim 1, wherein the HPV is an HPV type 6, 11, 16, 18, 26, 31, 33, 35, 39, 42, 44, 45, 51, 52, 53, 56, 58, 59, 66, 68, 73, and/or 82.

8. The method of claim 1, wherein the HPV-associated disease comprises a tumor that is unresponsive to treatment only with an immune checkpoint inhibitor.

9. The method of claim 1, furthering comprising delivering to the subject a PD-L1 inhibitor, or a CTLA-4 inhibitor.

10. The method of claim 1, wherein the AMD3100 and the immune checkpoint inhibitor are delivered simultaneously.

11. The method of claim 1, wherein the AMD3100 and the immune checkpoint inhibitor are delivered sequentially.

12. The method of claim 1, wherein the immune checkpoint inhibitor is delivered at a dose of about 0.1 mg/kg body weight per day to about 50 mg/kg per day.

13. The method of claim 1, wherein the method consists of delivering to the subject:
    (a) a therapeutically effective amount of AMD3100; and
    (b) an immune checkpoint inhibitor selected from nivolumab and pembrolizumab.

* * * * *